(12) United States Patent
Finkelstein

(10) Patent No.: US 7,117,097 B2
(45) Date of Patent: Oct. 3, 2006

(54) METHODS, COMPUTER SOFTWARE PRODUCTS AND SYSTEMS FOR CORRELATING GENE LISTS

(75) Inventor: David Finkelstein, San Mateo, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 10/319,150

(22) Filed: Dec. 13, 2002

(65) Prior Publication Data

US 2004/0115646 A1    Jun. 17, 2004

(51) Int. Cl.
*G06F 17/00* (2006.01)

(52) U.S. Cl. .............................. 702/19; 702/20; 435/6

(58) Field of Classification Search .................. 702/19, 702/20
See application file for complete search history.

(56) References Cited

OTHER PUBLICATIONS van Zyl et al, Comparative and Functional Genomics 3: 306 (2002).*
Anonymous, http://ccgb.umn.edu/support/software/gspring/Help-Pages/GSUM-120.html.*

\* cited by examiner

*Primary Examiner*—James Martinell
(74) *Attorney, Agent, or Firm*—Affymetrix, Inc.

(57) ABSTRACT

In some embodiment of the invention, methods are provided to compare lists of genes. In one embodiment, the genes are ranked with the lists. The ranks are analyzed using Spearman correlation.

12 Claims, 2 Drawing Sheets

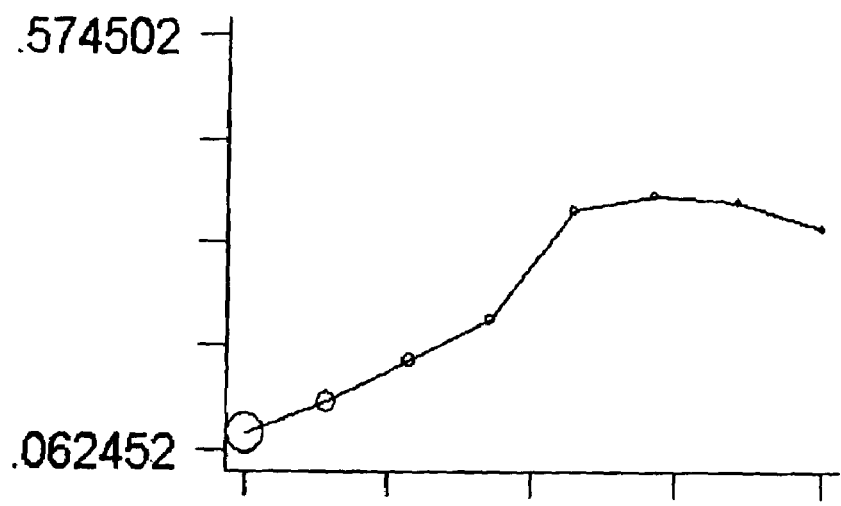

user==3 user==4 user==5

METHODS, COMPUTER SOFTWARE PRODUCTS AND SYSTEMS FOR CORRELATING GENE LISTS

FIELD OF INVENTION

This invention is related to bioinformatics, computer software and computer systems.

BACKGROUND OF THE INVENTION

Massive parallel gene expression monitoring experiments generate unprecedented amounts of information. Effective analysis of the large amount of data may lead to the development of new drugs and new diagnostic tools. Therefore, there is a great demand in the art for methods for organizing, accessing and analyzing the vast amount of information collected using massive parallel gene expression monitoring methods.

SUMMARY OF THE INVENTION

In one aspect of the invention, methods, computer software products and systems are provided for comparing two or more lists of the genes. The genes are ranked according to certain criteria, such as the statistic significance of their expression change, the magnitude of expression change, etc. The Spearman Correlation is calculated for the common genes in the lists. A higher Spearman Correlation indicates the similarity between the lists.

In some embodiments, the methods are used to analyze the similarity between gene expression data sets. For example, gene expression profiles obtained from different laboratories may be compared using Spearman Correlation calculated using the ranks of genes based upon their statistical significance. In one particular preferred embodiment, data about gene expression changes from several sources, such as several laboratories, are analyzed, genes are ranked based upon their statistical significance with each laboratory. To compare a first laboratory with the other laboratories, a list of genes are selected based upon a threshold (such as the P-value) as significantly changed for the first laboratory. The ranks of the genes in each of the lists are used to calculate a Spearman Correlation, which indicates the correlation of the results obtained from the different laboratories. These pair wise correlations can then be averaged or summed. The sum or average correlation can be calculated for a series of thresholds and plot against the threshold of the number of genes used to generate correlations.

Another aspect of the invention is that the Spearmen Correlation vs. threshold graph (see, e.g., FIG. 1) can be used to select the lowest p value reasonable where rank correlation is well preserved. In one embodiment, the reasonable p value may be determined for a single list where correlations are performed between subsets of data, as in leave one out cross validation techniques.

In yet another aspect of the invention, the methods for analyzing the similarity between gene lists may be used for pattern detection for gene expression data analysis and for diagnostic applications. In one preferred embodiment, the expression of a large number of genes in patient sample is detected. The expression is compared with a reference normal sample (which is not associated with the disease to be diagnosed) to detect differences in gene expression. The genes (some genes of the group or all detected genes) are then ranked according to their expression differences. In addition, reference ranks of genes for a particular disease is provided. The reference ranks may be obtained by comparing known disease sample with a normal sample. The genes may be ranked according to their difference in expression to obtain the reference ranks.

A Spearman Correlation is then calculated using the ranks of the genes and the reference ranks. A high Spearman Correlation value, such as greater than 0.9, 0.8, 0.7, 0.6, or 0.5, may indicate the patient's gene expression profiles is similar to that of a disease reference sample and the patient may has this particular disease.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE INVENTION

Figure 1:
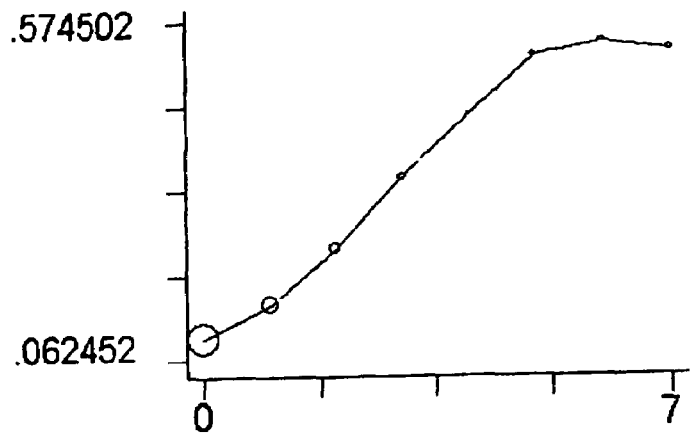
FIG. 1 shows the average Spearman correlation coefficients vs. threshold values for determining the significance of genes.
Figure 1:
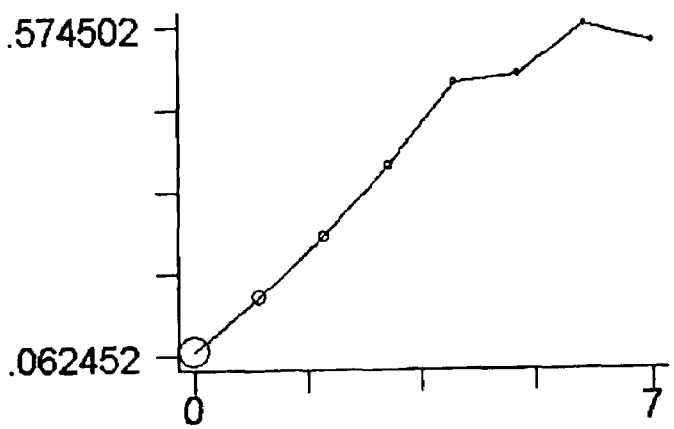
Figure 1:
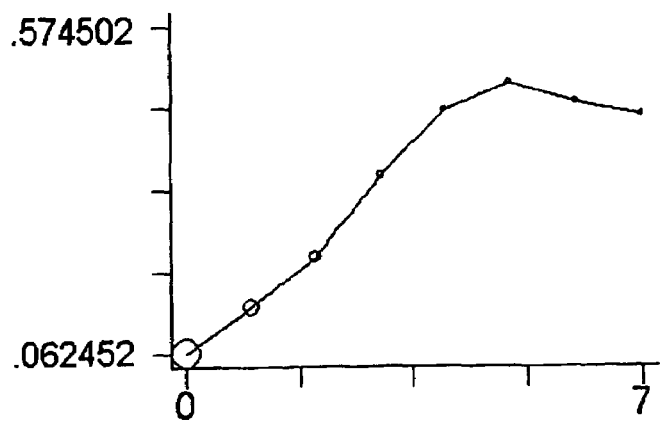

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

I. General

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I–IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, New York, Gait, "Oligonucleotide Synthesis: A Practical Approach" 1984, IRL Press, London, Nelson and Cox (2000), Lehninger, Principles of Biochemistry 3rd Ed., W.H. Freeman Pub., New York, N.Y. and Berg et al. (2002) Biochemistry, 5th Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285, which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays which are also described.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring, and profiling methods are shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 60/319,253, 10/013,598, and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, e.g., PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070 and U.S. patent application Ser. No. 09/513,300, which are incorporated herein by reference.

Other suitable amplification methods include the ligase chain reaction (LCR) (e.g., Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., Genome Research 11, 1418 (2001), in U.S. Pat. Nos. 6,361,947, 6,391,592 and U.S. patent application Ser. Nos. 09/916,135, 09/920,491, 09/910,292, and 10/013,598, which are incorporated herein by reference for all purposes.

Methods for conducting polynucleotide hybridization assays have been well developed in the art. Hybridization assay procedures and conditions will vary depending on the application and are selected in accordance with the general binding methods known including those referred to in: Maniatis et al. Molecular Cloning: A Laboratory Manual (2nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davism, P.N.A.S, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800, 992, 5,834,758; 5,856,092, 5,902,723, 5,936,324, 5,981, 956, 6,025,601, 6,090,555, 6,141,096, 6,185,030, 6,201, 639; 6,218,803; and 6,225,625, in U.S. Patent application Ser. No. 60/364,731 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170, which are incorporated herein by reference.

Additionally, the present invention may have preferred embodiments that include methods for providing genetic information over networks such as the Internet as shown in U.S. patent application Ser. Nos. 10/063,559, 60/349,546, 60/376,003, 60/394,574, 60/403,381.

II. Glossary

The following terms are intended to have the following general meanings as used herein.

Nucleic acids according to the present invention may include any polymer or oligomer of pyrimidine and purine bases, preferably cytosine (C), thymine (T), and uracil (U), and adenine (A) and guanine (G), respectively. See Albert L. Lehninger, PRINCIPLES OF BIOCHEMISTRY, at 793–800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be deoxyribonucleic acid (DNA) or ribonucleic acid (RNA), or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA), which may be isolated from natural sources, recombinantly produced or artificially synthesized and mimetics thereof. A further example of a polynucleotide of the present invention may be peptide nucleic acid (PNA) in which the constituent bases are joined by peptides bonds rather than phosphodiester linkage, as described in Nielsen et al., Science 254: 1497–1500 (1991), Nielsen Curr. Opin. Biotechnol., 10:71–75 (1999). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

An "array" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports.

A nucleic acid library or array is an intentionally created collection of nucleic acids which can be prepared either synthetically or biosynthetically in a variety of different formats (e.g., libraries of soluble molecules; and libraries of oligonucleotides tethered to resin beads, silica chips, or other solid supports). Additionally, the term "array" is meant to include those libraries of nucleic acids which can be prepared by spotting nucleic acids of essentially any length (e.g., from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases (see, e.g., U.S. Pat. No. 6,156,501, incorporated herein by reference). The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleotide sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

"Solid support", "support", and "substrate" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations.

Combinatorial Synthesis Strategy: A combinatorial synthesis strategy is an ordered strategy for parallel synthesis of diverse polymer sequences by sequential addition of reagents which may be represented by a reactant matrix and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids. See, e.g., U.S. Pat. No. 5,143,854.

Monomer: refers to any member of the set of molecules that can be joined together to form an oligomer or polymer. The set of monomers useful in the present invention includes, but is not restricted to, for the example of (poly) peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either subunit alone.

Biopolymer or biological polymer: is intended to mean repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above. "Biopolymer synthesis" is intended to encompass the synthetic production, both organic and inorganic, of a biopolymer.

Related to a bioplymer is a "biomonomer" which is intended to mean a single unit of biopolymer, or a single unit which is not part of a biopolymer. Thus, for example, a nucleotide is a biomonomer within an oligonucleotide biopolymer, and an amino acid is a biomonomer within a protein or peptide biopolymer; avidin, biotin, antibodies, antibody fragments, etc., for example, are also biomonomers. Initiation Biomonomer: or "initiator biomonomer" is meant to indicate the first biomonomer which is covalently attached via reactive nucleophiles to the surface of the polymer, or the first biomonomer which is attached to a linker or spacer arm attached to the polymer, the linker or spacer arm being attached to the polymer via reactive nucleophiles.

Complementary: Refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

The term "hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid." The proportion of the population of polynucleotides that forms stable hybrids is referred to herein as the "degree of hybridization".

Hybridization conditions will typically include salt concentrations of less than about 1M, more usually less than about 500 mM and less than about 200 mM. Hybridization temperatures can be as low as 5° C., but are typically greater than 22° C., more typically greater than about 30° C., and preferably in excess of about 37° C. Hybridizations are usually performed under stringent conditions, i.e. conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the thermal melting point (Tm) fro the specific sequence at a defined ionic strength and pH. The Tm is the temperature (under defined ionic strength, pH and nucleic acid composition) at which 50% of the probes complementary to the target sequence hybridize to the target sequence at equilibrium.

Typically, stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM NaPhosphate, 5 mM EDTA, pH 7.4) and a temperature of 25–30° C. are suitable for allele-specific probe hybridizations. For stringent conditions, see for example, Sambrook, Fritsche and Maniatis. "Molecular Cloning A laboratory Manual" 2nd Ed. Cold Spring Harbor Press (1989) and Anderson "Nucleic Acid Hybridization" 1st Ed., BIOS Scientific Publishers Limited (1999), which are hereby incorporated by reference in its entirety for all purposes above.

Hybridization probes are nucleic acids (such as oligonucleotides) capable of binding in a base-specific manner to a complementary strand of nucleic acid. Such probes include peptide nucleic acids, as described in Nielsen et al., Science 254:1497–1500 (1991), Nielsen Curr. Opin. Biotechnol., 10:71–75 (1999) and other nucleic acid analogs and nucleic acid mimetics. See U.S. Pat. No. 6,156,501.

Probe: A probe is a molecule that can be recognized by a particular target. In some embodiments, a probe can be surface immobilized. Examples of probes that can be investigated by this invention include, but are not restricted to, agonists and antagonists for cell membrane receptors, toxins and venoms, viral epitopes, hormones (e.g., opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

Target: A molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

Ligand: A ligand is a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (e.g., opiates, steroids, etc.), hormone receptors, peptides, enzymes, enzyme substrates, substrate analogs, transition state analogs, cofactors, drugs, proteins, and antibodies.

Receptor: A molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to those molecules shown in U.S. Pat. No. 5,143,854, which is hereby incorporated by reference in its entirety.

Effective amount refers to an amount sufficient to induce a desired result.

mRNA or mRNA transcripts: as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, a cRNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

A fragment, segment, or DNA segment refers to a portion of a larger DNA polynucleotide or DNA. A polynucleotide, for example, can be broken up, or fragmented into, a plurality of segments. Various methods of fragmenting nucleic acid are well known in the art. These methods may be, for example, either chemical or physical in nature. Chemical fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave DNA at known or unknown locations. Physical fragmentation methods may involve subjecting the DNA to a high shear rate. High shear rates may be produced, for example, by moving DNA through a chamber or channel with pits or spikes, or forcing the DNA sample through a restricted size flow passage, e.g., an aperture having a cross sectional dimension in the micron or submicron scale. Other physical methods include sonication and nebulization. Combinations of physical and chemical fragmentation methods may likewise be employed such as fragmentation by heat and ion-mediated hydrolysis. See for example, Sambrook et al., "Molecular Cloning: A Laboratory Manual," 3rd Ed. Cold Spring Harbor Laboratory Press, Cold Spring Harbor, N.Y. (2001) ("Sambrook et al.) which is incorporated herein by reference for all purposes. These methods can be optimized to digest a nucleic acid into fragments of a selected size range. Useful size ranges may be from 100, 200, 400, 700 or 1000 to 500, 800, 1500, 2000, 4000 or 10,000 base pairs. However, larger size ranges such as 4000, 10,000 or 20,000 to 10,000, 20,000 or 500,000 base pairs may also be useful. See, e.g., Dong et al., Genome Research 11, 1418 (2001), in U.S. Pat. Nos. 6,361,947, 6,391,592, incorporated herein by reference.

A primer is a single-stranded oligonucleotide capable of acting as a point of initiation for template-directed DNA synthesis under suitable conditions e.g., buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

A genome is all the genetic material of an organism. In some instances, the term genome may refer to the chromosomal DNA. Genome may be multichromosomal such that the DNA is cellularly distributed among a plurality of individual chromosomes. For example, in human there are 22 pairs of chromosomes plus a gender associated XX or XY pair. DNA derived from the genetic material in the chromosomes of a particular organism is genomic DNA. The term genome may also refer to genetic materials from organisms that do not have chromosomal structure. In addition, the term genome may refer to mitochondria DNA. A genomic library is a collection of DNA fragments represents the whole or a portion of a genome. Frequently, a genomic library is a collection of clones made from a set of randomly generated, sometimes overlapping DNA fragments representing the entire genome or a portion of the genome of an organism.

An allele refers to one specific form of a genetic sequence (such as a gene) within a cell or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations". At each autosomal specific chromosomal location or "locus" an individual possesses two alleles, one inherited from the father and one from the mother. An individual is "heterozygous" at a locus if it has two different alleles at that locus. An individual is "homozygous" at a locus if it has two identical alleles at that locus.

Polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

Single nucleotide polymorphism (SNPs) are positions at which two alternative bases occur at appreciable frequency (>1%) in the human population, and are the most common type of human genetic variation. The site is usually preceded by and followed by highly conserved sequences of the allele (e.g., sequences that vary in less than 1/100 or 1/1000 members of the populations). A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

Genotyping refers to the determination of the genetic information an individual carries at one or more positions in the genome. For example, genotyping may comprise the determination of which allele or alleles an individual carries for a single SNP or the determination of which allele or alleles an individual carries for a plurality of SNPs. A genotype may be the identity of the alleles present in an individual at one or more polymorphic sites.

Linkage disequilibrium or allelic association means the preferential association of a particular allele or genetic marker with a specific allele, or genetic marker at a nearby chromosomal location more frequently than expected by chance for any particular allele frequency in the population. For example, if locus X has alleles a and b, which occur equally frequently, and linked locus Y has alleles c and d, which occur equally frequently, one would expect the combination ac to occur with a frequency of 0.25. If ac occurs more frequently, then alleles a and c are in linkage disequilibrium. Linkage disequilibrium may result from natural selection of certain combination of alleles or because an allele has been introduced into a population too recently to have reached equilibrium with linked alleles. A marker in linkage disequilibrium can be particularly useful in detecting susceptibility to disease (or other phenotype) notwithstanding that the marker does not cause the disease. For example, a marker (X) that is not itself a causative element of a disease, but which is in linkage disequilibrium with a gene (including regulatory sequences) (Y) that is a causative element of a phenotype, can be detected to indicate susceptibility to the disease in circumstances in which the gene Y may not have been identified or may not be readily detectable.

III. Correlating Between Lists of Genes

In one aspect of the invention, methods, systems and computer software products are provided for conducting biological analysis. The methods, systems and computer software products are particularly suitable for analyzing gene expression data preferably obtained using microarray technology. However, the methods, systems and computer software products are also suitable for analyzing other types of biological data, such as protein profile data.

DNA microarray technology has been extensively applied for studing the expression of a large number of genes. In a typical experiment, the expression of thousands or tens of thousands of genes is monitored to detect the changes between treatments (disease vs. normal, different physiological states, toxicological, pharmacological changes, etc.). Such experiments interrogate the changes between biological states. For a description of methods for monitoring the expression of genes in different biological states, see, e.g., U.S. Pat. Nos. 5,800,992, 6,309,822, incorporated herein by reference.

The biological state of a biological sample (such as a cell, a biopsy tissue sample, serum sample, etc.) can be represented by the expression of a list of genes. A collection of the values of gene expression is generally referred to as the "gene expression profile" of the biological state of a sample. Methods for using gene expression profiling in drug discovery are disclosed in, for example, U.S. Pat. No. 6,333,155, incorporated herein by reference.

Two or more biological states are typically compared by examining the profiles to discover changed biological variables. For example, cells may be treated with a drug and the expression of genes in treated and untreated cells can be compared to detect genes whose expression is altered.

It is well known to one of the skill in the art that statistical analysis can be used to detect any changes in biological variables. Experimental design and statistical analysis methods are the subject of numerous books including, e.g., Abrahamse, A. 1969, The Power of Some Tests in the General Linear Model University of Rotterdam; Aczel, A. 1995 Statistics: Concepts and Applications Richard D. Irwin Inc.; Agresti, A. 1990 Categorical Data Analysis John Wiley and Sons, New York; Aickin, M. 1983 Linear Statistical Analysis of Discrete Data Wiley, New York; Aitchison, J. 1997 Statistical Concepts and Applications in Medicine Chapman and Hall; Anderson, A. 1989 Interpreting Data: A First Course in Statistics Chapman and Hall/CRC; Anderson, T. 1986 The Statistical Analysis of Data (Second Edition) Scientific Press; Anderson, T. & Finn, J. 1996 The New Statistical Analysis of Data Springer, New York; Anderson, V. L. & McLean, R. A. 1974 Design of Experiments: A Realistic Approach Marcel Dekker, New York; Backhouse, J. 1967 Statistics: An Introduction to Tests of Significance Longmans, London; Bailey, N. T. J. 1981 Statistical Methods in Biology (Second Edition) Hodder and Stoughton, London; Bechhofer, R., Santner, T., & Goldsman, D. 1995 Design and Analysis of Experiments for Statistical Selection, Screening, and Multiple Comparisons Wiley, New York; Behnen, K. & Neuhaus, G. 1989 Rank Tests with Estimated Scores and Their Application B. G. Tuebner, Stuttgart; Brandt, S. 1999 Data Analysis Statistical and Computational Methods for Scientists and Engineers (with CD-ROM) New York, Springer; Campbell, R. 1989 Statistics for Biologists Cambridge University Press; Dean, A. & Voss, D. 1999 Design and Analysis of Experiments Springer, New York; Federer, W. 1955 Experimental Design, Theory and Application Macmillan, New York; Garcia-Diaz, A. & Phillips, D. 1995 Principles of Experimental Design and Analysis Chapman & Hall, London; Harlow, L., Mulaik, S. & Steiger, J. 1997 What if There Were No Significance Tests? Lawrence Erlbaum Associates, Publishers; Snedecor, G. W. & Cochran, W. G. 1980 Statistical Methods (Seventh Edition) Iowa State University Press, Iowa; Yandell, B. 1997 Practical Data Analysis for Designed Experiments CRC Press; Yates, F. 1970 Experimental Design: Selected Papers of Frank Yates Griffin, London; Zar, J. 1999 Biostatistical Analysis Prentice-Hall, Engelwood Cliffs; Zolman, J. F. 1993 Biostatistics. Experimental Design and Statistical Inference Oxford University Press, Oxford, all incorporated herein by reference. Computer algorithms, software and source code for carrying out various statistical analysis are widely available.

Gene expression values are typically analyzed using standard statistical methods by, e.g., calculating a statistically significant cut-off, such as a p-value from a t-test, an ANOVA or a nonparametric test, for measurements that have changed between experimental conditions. A list of significantly changed gene can be generated after such statistical tests. It is apparent to one of skill in the art that the list is dependent upon the threshold value used to determine whether the expression of a gene is significantly altered.

In one aspect of the invention, methods, computer software products and systems are provided to evaluate the similarity of the lists. In some embodiments, the gene lists are ranked and then, a Spearman's Correlation coefficient is calculated based upon the ranks to evaluate the similarity.

Spearman Correlation can be thought of as the regular Pearson product-moment correlation coefficient (Pearson r); that is, in terms of the proportion of variability accounted for, except that Spearman Correlation is computed from ranks. Detailed discussions of the Spearman Correlation statistic, its power and efficiency can be found in Gibbons (1985), Nonparametric Statistical Inference (2nd ed.). New York: Marcel Dekker; Hays (1981), Statistics (3rd ed.). New York: CBS College Publishing; McNemar (1969), Psychological Statistics (4th ed.). New York: Wiley; Siegel (1956), Nonparametric Statistics for the Behavioral Sciences. New York: McGraw-Hill; Siegel and Castellan (1988), Nonparametric Statistics for the Behavioral Sciences (2nd ed.) New York: McGraw-Hill, all incorporated herein by reference.

In one aspect of the invention, methods, computer software products and systems are provided for comparing two or more lists of the genes. The genes are ranked according certain criteria, such as the statistic significance of their expression change, the magnitude of expression change, etc. The Spearman Correlation is calculated for the common genes in the lists. A higher Spearman Correlation indicates the similarity between the lists.

In some embodiments, the methods are used to analyze the similarity between gene expression data sets. For example, gene expression profiles obtained from different laboratories may be compared using Spearman Correlation calculated using the ranks of genes based upon their statistical significance. In one particular preferred embodiment, data about gene expression changes from several laboratories are analyzed, genes are ranked based upon their statistical significance with each laboratory. To compare a first laboratory with the other laboratories, a list of genes are selected based upon a threshold (such as the P-value) as significantly changed for the first laboratory. The ranks of the genes in each of the lists are used to calculate pair wise Spearman Correlation, which indicates the correlation of the results obtained from the different laboratories.

In another aspect of the invention, the methods for analyzing the similarity between gene lists may be used for pattern detection for gene expression data analysis and for diagnostic applications. In one preferred embodiment, the expression of a large number of genes in patient sample is detected. The expression is compared with a reference normal sample (which is not associated with the disease to be diagnosed) to detect differences in gene expression. The genes (some genes of the group or all detected genes) are then ranked according to their expression differences. In addition, reference ranks of genes for a particular disease is provided. The reference ranks may be obtained by comparing known disease sample with a normal sample. The genes may be ranked according to their difference in expression to obtain the reference ranks.

A software product of invention typically includes a computer readable medium, such as CD-ROM or a DVD Rom disk. Software codes that execute the method steps of the invention are stored in the computer readable medium. Software of the invention can be written in any suitable language including C/C++, Java, C#. Basic, Fortran, Perl, etc. In yet another aspect of the invention, systems for analyzing biological data are provided. In some embodiments, the system includes a central processing unit (CPU) and coupled with the CPU is a memory unit. The system executes the methods steps of the invention.

IV. Example

This example illustrates an exemplary application of the methods of the invention. The expression of a large number of genes were monitored in several experiments (may be in different laboratories or users). The data from the different users were compared.

The statistical method was designed to limit false positives by use of a threshold p-value. As most probe sets (each probe set typically detects transcript(s) from one gene) in disagreement are probable false negatives, it is expected to see that significant p-values obtained in one experiment are correlated with significant p-values obtained in duplicated experiments.

In this example (FIG. 1), gene expression data from five users were compared. Pair wise Spearman correlations between User 1 and other users were calculated and averaged. The resulting average correlation vs. the threshold for inclusion of genes is shown in FIG. 1A. Similarly, results for User 2-User % are shown in FIG. 1B–1E.

The threshold is based on –ln(p-value). For example, for the 0 threshold all 8799 genes were selected and ranked for each user. The rank of site 1 was then compared to the ranks of sites 2, 3, 4 & 5 respectively. Each comparison gives a correlation, ρ(rho) and all the ρs are averaged. This averaged ρ for 0 is plotted as the first data point on the first graph. To plot the second data point, the threshold for user 1 is incremented to 1. (A threshold of 1 means that all probe sets that have a –ln(p-value for user 1)>1 are selected.) The resulting list of probe sets is then ranked and compared to the ranked lists of all other users and the ρs averaged.

If the order of probesets (each probe set typically detects transcript(s) from one gene) between two ranked lists is equivalent, then the correlation is high (near 1). All pair wise rank correlations are then averaged with increasing thresholds. For example, for the 0 threshold all 8799 genes were selected and ranked for each user. The rank of site 1 was then compared to the ranks of sites 2, 3, 4 & 5 respectively. Each comparison gives a correlation, ρ (rho) and all the ρs are averaged. This averaged ρ for 0 is plotted as the first data point (1A). To plot the second data point, the threshold for user 1 is incremented to 1. (A threshold of 1 means that all probe sets that have a –ln(p-value for user 1)>1 are selected.) The resulting list of probe sets is then ranked and compared to the ranked lists of all other users and the ρs averaged as before. As more statistically significant probesets are chosen, agreement (based on average ρ) increases until a plateau is reached. If the threshold is extended even further the correlations drop in some cases, due in part to the ever shrinking number of genes examined.

| Threshold | Observations |
| --- | --- |
| 7 | 46 |
| 6 | 73 |
| 5 | 137 |
| 4 | 247 |
| 3 | 531 |
| 2 | 1243 |
| 1 | 3204 |
| 0 | 8799 |

Probesets that pass the pscore_1 = –ln(p-value user 1).

The results represent a substantial improvement in the list of significant genes and a more realistic representation of the actual agreement of the probesets between the different lists.

It is to be understood that the above description is intended to be illustrative and not restrictive. Many variations of the invention will be apparent to those of skill in the art upon reviewing the above description. The scope of the invention should be determined with reference to the appended claims, along with the full scope of equivalents to which such claims are entitled. All cited references, including patent and non-patent literature, are incorporated herewith by reference in their entireties for all purposes.

What is claimed is:

1. A computer implemented method for comparing a plurality of gene expression data sets comprising:
    Providing at least two lists of genes, wherein the lists are obtained from different laboratories;
    Ranking the genes within each list;
    Calculating the Spearman Correlation for the ranks of the genes that are common to more than one list.

2. The method of claim 1 wherein the list of genes comprises at least 100 genes.

3. The method of claim 2 wherein the list of genes comprises at least 1000 genes.

4. The method of claim 1 wherein the plurality of lists comprises at least three lists.

5. The method of claim 4 wherein the Spearman correlation is a pair wise Spearman correlations between the lists.

6. The method of claim 5 further comprising avenging the pair wise Spearman Correlations.

7. A computer implemented method for diagnosing a disease comprising:
    Obtaining gene expression values from a patient sample;
    Comparing the patient sample with a reference sample to detect gene expression changes;
    Ranking the genes according to the expression changes; and
    Calculating Spearman Correlation between the ranks of the genes in the patient sample and reference ranks of genes in a disease reference sample.

8. A computer readable medium having software modules for performing the method of:
    providing at least two lists of genes, wherein the lists are obtained from different laboratories;
    ranking the genes within each list;
    calculating the Spearman Correlation for the ranks of the genes that are common to more than one list.

9. The computer readable medium of claim 8 wherein the plurality of lists comprises at least three lists.

10. The computer readable medium of claim 9 wherein the Spearman correlation is a pair wise Spearrnan correlations between the lists.

11. The computer readable medium of claim 10 further comprising averaging the pair wise Spearman Correlations.

12. A computer readable medium having software modules for performing the method of:
    obtaining gene expression values from a patient sample;
    comparing the patient sample with a reference sample to detect gene expression changes;
    ranking the genes according to the expression changes; and
    calculating Speanran Correlation between the ranks of the genes in the patient sample and reference ranks of genes in a disease reference sample.

* * * * *